United States Patent [19]

Levin et al.

[11] Patent Number: 5,166,193
[45] Date of Patent: Nov. 24, 1992

[54] METHOD FOR KILLING PESTS

[75] Inventors: Gilbert V. Levin, Annapolis; Lee R. Zehner, Brookeville, both of Md.

[73] Assignee: Biospherics Incorporated, Beltsville, Md.

[21] Appl. No.: 350,902

[22] Filed: May 12, 1989

[51] Int. Cl.$^5$ ............................................. A01N 43/04
[52] U.S. Cl. .............................. 514/23; 424/DIG. 10; 424/DIG. 11; 514/918
[58] Field of Search .................. 514/23, 918; 536/1.1; 424/DIG. 10, DIG. 11

[56] References Cited

U.S. PATENT DOCUMENTS

| 4,262,032 | 4/1981 | Levin | 426/658 |
| 4,279,895 | 7/1981 | Carle | 424/660 |
| 4,371,616 | 2/1983 | Huibers | 536/1.1 X |
| 4,386,071 | 5/1983 | Carle | 424/660 |
| 4,786,722 | 11/1988 | Zehner | 536/1.1 |

Primary Examiner—John W. Rollins
Attorney, Agent, or Firm—Roylance, Abrams, Berdo & Goodman

[57] ABSTRACT

There is disclosed a method for killing pests, especially insects, which comprises exposing the pests to, and permitting said pests to ingest, a substance which is either not transported or which is poorly transported across the digestive tract membranes of the pests.

8 Claims, No Drawings

METHOD FOR KILLING PESTS

BACKGROUND OF THE INVENTION

This invention relates to the use of non- or low-metabolizable substances to kill pests, especially insects.

Pesticides in common use depend upon general or specific toxicity of one or more ingredients to one or more species, or groups, of pests. In many instances, broad or specific pest attractants, ranging from relatively simple odorants to pheromones, are incorporated into the pesticide to induce the pests to take the bait including the active pesticide ingredients.

Unfortunately, in most cases, the antimetabolic or toxic effects which make the pesticides effective may also be effective against desirable species, including man, when ingested or inhaled. Lethal human exposures have occurred to workers manufacturing pesticide ingredients, workers combining active ingredients with attractants and/or packaging the product, pesticide applicators in fields or buildings and bystanders inadvertently exposed or who ingested the pesticides deliberately, as in the case of children, or accidently without knowing the effects. Another classic problem with many pesticides is the gradual adaptation of the pests rendering them immune or resistant.

Pesticides also find their way into surface waters and groundwater as the result of extensive broadcasting of these materials in combating infestations of pests or in preventing pests from achieving destructive or nuisance levels in numbers. In recent years, increasing attention has been paid to the effect of such chemical contamination of surface or subsurface derived potable waters. Some such pesticides can travel great distances in surface or subsurface waters and can persist at concentrations harmful to man. Accordingly, the EPA and other agencies have established toxicity levels for these materials which must not be exceeded in food and potable waters. The limits imposed result from the typical risk/benefit ratio type of analysis for which accurate scientific and economic parameters are difficult to establish.

U.S. Pat. Nos. 4,279,895 and 4,386,071, both to Carle, disclose insecticidal compositions based on diatomaceous silica and a sugar. The '895 patent states that the insect is attracted to the composition by the sugar which is impregnated in the pores of the diatomaceous silica. The insects thereafter swallow the composition because they are attracted to the sugar. Tests on dead insects after eating the composition reveal that their bowels are perforated, which results in rapid death followed by desiccation. The active agent in this case is the diatomaceous silica.

It is an object of this invention to avoid hazards to humans and other beneficial, desirable species while still providing adequate pest control and doing so through a mechanism against which adaptive immunity is extremely unlikely or impossible.

SUMMARY OF THE INVENTION

In accordance with this invention, there is provided a method for killing pests, especially insects, which comprises exposing said pests to, and permitting said pests to ingest, a substance which is either not transported or which is poorly transported across the digestive tract membranes of said pests, and which causes an osmotically driven influx of water into the digestive tract of said pests. This results in death to the pests by dehydration, organic or structural dysfunction, or disruption, or any combination thereof; or, in some instances, death may occur through starvation by virtue of preference of the pest for the substance which is non-metabolized or only slightly metabolized.

DETAILED DESCRIPTION OF THE INVENTION

This invention provides a convenient, easily deployed, mammalian non-toxic method for causing death in a wide variety of pests, especially insects. The active ingredient(s) can be manufactured, handled, packaged and dispensed by humans with no toxic hazard to themselves or to anyone inadvertently or purposely ingesting or inhaling the substance(s). The method of destroying insects is not through specific or direct toxicity, but through the creation of high osmotic pressure differentials which cause death through electrolyte imbalance, dehydration, or rupture of organs, or any combination thereof. This is accomplished through ingestion of the pesticide by the target organism over a period of days. The active ingredient of the pesticide is generally one or more non-metabolizable or only slightly metabolizable carbohydrates of relatively low molecular weight resulting from their having fewer than 12 carbon atoms per molecule, although there are exceptions which permit larger molecules to be used in the practice of this invention. The pests consume the substance because the active ingredient is sweet and attractive or, if the active ingredient itself is not sweet, a sweetening agent is incorporated into the pesticide. The substance which is either not transported, poorly transported, or not actively diffused across the digestive tract membranes of the pests is generally selected from among low-molecular weight carbohydrates with such properties. Because they remain inside the intestinal tract and are relatively small molecules, they create osmotic pressure which can only be equilibrated by the movement of water from the rest of the pest body into the intestinal tract. This results in the excretion of large amounts of water and/or damage to internal organs with death occurring from dehydration and/or structural damage.

The active substance used in the practice of this invention, i.e., the substance which is either not transported or which is poorly transported across the digestive tract membranes of the pest upon ingestion, and which causes an osmotically driven influx of water into the intestines, may be a low molecular weight organic compound of low or non-metabolizability, or a low to moderate molecular weight compound of non- or low-degradability and non- or low-transportability across the digestive tract membranes. Such compounds include all L-hexoses except sorbose, which occurs naturally in the L-form and is metabolized, other L-sugars containing no more than 12 carbon atoms, alditols (L- and D-) containing no more than 12 carbon atoms, oligosaccharides and 4-carbon sugar alcohols, including but not limited to Palatinit (an equimolar mixture of α-D glucopyranosyl-(1→6)-mannitol and α-D-glucopyranosyl-(1→6)-sorbitol), maltitol, lactitol, mannitol, hydrogenated starch hydrolysates and erythritol, all of which have been demonstrated to be non-metabolized or little metabolized. In addition, the active substance may be a larger molecule with demonstrated capability to exert high osmotic pressure, such as Neosugar (a mixture of oligosaccharides commonly called fructooligosaccharides and commonly comprised of three sugars, i.e., 1-kestose, nystose, and $1^F$-β-fructofuranosyl nystose in various proportions, depending on method of production) and Polydextrose (various polymers of D-glucose, citric acid and sorbitol). Specific examples of active substances which may be used in the practice of this invention include L-allose, L-altrose, L-glucose, L-mannose, L-gulose, L-idose, L-galactose, L-talose, L-fructose, L-fucose, L-psicose, L-rhamnose, L-tagatose, L-sorbitol, L-mannitol, dulcitol, L-talitol, L-iditol, D-mannitol, D-iditol, D-gulose, D-sorbose, D-tagatose, Neosugar, meso-erythritol, D-threitol, L-threitol, and Polydextrose.

The active substances may be administered in the method of this invention in any manner, e.g., they may be placed in open or partially closed containers which provide or limit access to pests such as insects; or they may be formulated into sprays or powders and applied to an animal to control pests such as fleas, or to crops or soil to control infestations of pests.

The active substances of this invention are not toxic to mammals or primates. Considerable safety evidence with respect to testing two or more animal species and humans exists for L-gulose, L-fructose, L-glucose, Polydextrose, Neosugar, xylitol, mannitol and maltitol, all of which have undergone toxicity testing and produced no effects at levels far exceeding those that would be encountered through use or accidental contact with the substances as pesticides. In addition, they have been found negative in Ames tests to detect carcinogenicity and in teratology tests.

The following examples illustrate the practice of this invention.

EXAMPLE 1

This experiment was performed with pogonomyrmex "Harvester" ants, workers only, in ant farms, 20 ants to a farm, obtained from U.M.I., Inc., Culver City, Calif. Each of four ant farms was activated per instructions and allowed to adjust to the environment for 48 hours. Then D-fructose was added to Farm 1 (the control), a mixture of D- and L-fructose was added to Farm 2, L-fructose was added to Farm 3, and L-glucose was added to Farm 4. These substances were added in aluminum boats fixed about two inches above the sand surface in each farm. The initial dose of each substance was 0.05 grams in separate 0.05 ml aliquots of aqueous solution. After the fifth day, an additional 0.01 gram of each substance in 0.5 ml aqueous solution was added to its respective boat. After the eighth day and daily thereafter, five drops of water were added to each farm. The numbers of living ants were counted each morning. The results are set forth in Table 1.

TABLE 1

| | Numbers of Ants Surviving L-Sugars | | | |
|---|---|---|---|---|
| Day | Farm 1 D-Fructose | Farm 2 D-/L-Fructose | Farm 3 L-Fructose | Farm 4 L-Glucose |
| 1 | 20 | 20 | 20 | 20 |
| 2 | 19 | 17 | 19 | 20 |
| 3 | — | — | — | — |
| 4 | — | — | — | — |
| 5 | 18 | 13 | 18 | 17 |
| 6 | 18 | 10 | 18 | 17 |
| 7 | 18 | 10 | 18 | 17 |
| 8 | 18 | 9 | 11 | 16 |
| 9 | 18 | 5 | 10 | 13 |
| 10 | 18 | 4 | 10 | 12 |
| 11 | — | — | — | — |
| 12 | 18 | 4 | 9 | 12 |
| 13 | 18 | 3 | 7 | 12 |

These results show that a significant number of ants died in Farms 2, 3 and 4, each of which contained an L-sugar, whereas an insignificant amount of ants died in Farm 1, the control group exposed to a fully metabolizable sugar.

EXAMPLE 2

In making a purification of L-gulose in the laboratory, some of the equipment contacting the L-gulose was allowed to remain uncleaned in a large open area. Several days later, a large number of flying type insects was observed dead in the area near the equipment.

EXAMPLE 3

Six different groups of approximately 50 adult house flies (*Musca domestica*) were maintained in separate five-gallon cages with a dish of water and a dish of test substance, and were allowed to feed ad libitum on the test substance for a maximum period of two weeks. Mortalities were monitored each evening. The test substances were as follows:

| Group | Test Substance |
|---|---|
| 1 | Crystalline D-sucrose (8 grams) - control |
| 2 | Mixture of powdered D-sucrose (4 grams) and powdered L-gulose (4 grams) |
| 3 | Powdered L-gulose (8 grams) |
| 4 | Separate dishes containing crystalline D-sucrose (4 grams) and L-gulose (4 grams) |
| 5 | Mixture of powdered D-sucrose (7.2 grams) and L-gulose (0.8 grams) |
| 6 | Powdered L-fructose (8 grams) |

The results are set forth in Table 2 which reports the number of live flies in each group for each day on test. Day 0 was the first day the test substance was available to the insects. The results shown in Table 2 illustrate the effectiveness of the L-sugars with reference to the Group 1 control. After two days, the respective survival rates of the test and control populations diverge with total kills by L-sugars solely occurring in about five days.

TABLE 2

| Day | Group 1 D-Sucrose | Group 2 D-Sucrose and L-Gulose (1:1) | Group 3 L-Gulose | Group 4 D-Sucrose; L-Gulose (separate dishes) | Group 5 D-Sucrose and L-Gulose (9:1) | Group 6 L-Fructose |
|---|---|---|---|---|---|---|
| 0 | 41 | 55 | 42 | 55 | 61 | 59 |
| 1 | 41 | 55 | 42 | 53 | 60 | 59 |
| 2 | 41 | 53 | 23 | 52 | 60 | 51 |
| 3 | 41 | 47 | 6 | 52 | 60 | 23 |
| 4 | 40 | 39 | 6 | 48 | 56 | 8 |
| 5 | 40 | 30 | 2 | 47 | 56 | 6 |

TABLE 2-continued

| Day | Group 1 D-Sucrose | Group 2 D-Sucrose and L-Gulose (1:1) | Group 3 L-Gulose | Group 4 D-Sucrose; L-Gulose (separate dishes) | Group 5 D-Sucrose and L-Gulose (9:1) | Group 6 L-Fructose |
|---|---|---|---|---|---|---|
| 6 | 40 | 28 | 0 | 43 | 54 | 0 |
| 7 | 36 | 18 | | 39 | 50 | |
| 8 | 35 | 4 | | 38 | 48 | |
| 9 | 33 | 0 | | 37 | 47 | |
| 10 | 34 | | | 38 | 41 | |
| 11 | 32 | | | 37 | 41 | |
| 12 | 32 | | | 37 | 34 | |
| 13 | 30 | | | 33 | 27 | |
| 14 | 30 | | | 33 | 23 | |

What is claimed is:

1. A method for killing pests which comprises exposing said pests to, and permitting said pests to ingest, a substance which is either not transported or which is poorly transported across the digestive tract membranes of said pests, and which causes an osmotically driven influx of water into the digestive tracts of said pests.

2. A method as defined in claim 1 wherein said pests are insects.

3. A method as defined in claim 1 wherein said substance is naturally sweet, thereby attracting pests and inducing them to consume the substance.

4. A method as defined in claim 1 wherein a sweetener or other attractant is added to the substance.

5. A method for killing pests which comprises exposing said pests to, and permitting said pests to ingest, an L-hexose other than L-sorbose.

6. A method as defined in claim 5 wherein said pests are insects.

7. A method for killing pests which comprises exposing said pests to, and permitting said pests to ingest, a substance selected from the group consisting of L-allose, L-altrose, L-glucose, L-mannose, L-gulose, L-idose, L-galactose, L-talose, L-fructose, L-fucose, L-psicose, L-rhamnose, L-tagatose, L-sorbitol, L-mannitol, dulcitol, L-talitol, L-iditol, D-mannitol, D-iditol, D-gulose, D-sorbose, D-tagatose, Neosugar, meso-erythritol, D-threitol, L-threitol, and Polydextrose.

8. A method as defined in claim 7 wherein said pests are insects.

* * * * *